(12) United States Patent
Tzor et al.

(10) Patent No.: US 9,546,142 B2
(45) Date of Patent: Jan. 17, 2017

(54) PROCESS FOR PREPARING ISOXAFLUTOLE

(71) Applicant: ADAMA AGAN LTD., Ashdod (IL)

(72) Inventors: Omer Tzor, Kiryat-Ono (IL); Michael Grabarnick, Meitar (IL)

( * ) Notice: Subject to any disclaimer, the term of this patent is extended or adjusted under 35 U.S.C. 154(b) by 0 days.

(21) Appl. No.: 15/029,063

(22) PCT Filed: Oct. 13, 2014

(86) PCT No.: PCT/IL2014/050898
§ 371 (c)(1),
(2) Date: Apr. 13, 2016

(87) PCT Pub. No.: WO2015/056265
PCT Pub. Date: Apr. 23, 2015

(65) Prior Publication Data
US 2016/0251323 A1    Sep. 1, 2016

Related U.S. Application Data

(60) Provisional application No. 61/891,464, filed on Oct. 16, 2013.

(51) Int. Cl.
*C07D 261/08* (2006.01)

(52) U.S. Cl.
CPC .................................. *C07D 261/08* (2013.01)

(58) Field of Classification Search
None
See application file for complete search history.

(56) References Cited

U.S. PATENT DOCUMENTS

| 5,747,424 A | 5/1998 | Roberts et al. |
| 2003/0055292 A1 | 3/2003 | Warren |
| 2005/0288516 A1 | 12/2005 | Warren |

FOREIGN PATENT DOCUMENTS

| WO | 9418179 A1 | 8/1994 |

OTHER PUBLICATIONS

Preliminary Report on Patentability for PCT/IL2014/050898 mailed Apr. 28, 2016, 9 pages.
International Search Report for PCT/IL2014/050898 mailed Jan. 23, 2015, 3 pages.
Written Opinion of the International Searching Authority for PCT/IL2014/050898 mailed Jan. 23, 2015, 7 pages.

*Primary Examiner* — Kamal Saeed
(74) *Attorney, Agent, or Firm* — Cantor Colburn LLP

(57) ABSTRACT

A process for preparing isoxaflutole of formula (I) wherein the process comprises: admixing (5-cyclopropyl-4-isoxazolyl)[2-(methylthio)-4-(trifluoromethyl)phenyl]-methanone of formula (II) with acetic acid, acetic anhydride and hydrogen peroxide in the presence of a strong acid.

19 Claims, No Drawings

PROCESS FOR PREPARING ISOXAFLUTOLE

This application is a national stage application of PCT/IL2014/050898, filed Oct. 13, 2014, which claims priority to U.S. Provisional Application 61/891,464, Oct. 16, 2013, both of which are hereby incorporated by reference in their entirety.

BACKGROUND OF THE PRESENT SUBJECT MATTER

Isoxaflutole, known by the chemical name 5-cyclopropyl-4-[2-methylsulfonyl-4-(trifluoromethyl)benzoyl]isoxazole, is represented by the following structural formula I:

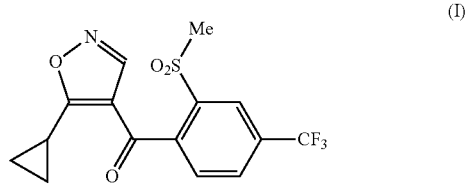 [SMILES: CS(=O)(=O)c1cc(C(F)(F)F)ccc1C(=O)c1cnoc1C1CC1]

(I)

Isoxaflutole is a p-hydroxyphenyl pyruvate dioxygenase inhibitor. This enzyme converts p-hydroxyphenyl pyruvate to homogentisate, a key step in plastoquinone biosynthesis. Inhibition of this enzyme leads to indirect inhibition of carotenoid biosynthesis, giving rise to chlorosis of new growth.

Isoxaflutole was first reported by B. M. Luscombe et al. (*Proc. Br. Crop Prot. Conf.—Weeds*, 1995, 1, 35).

The oxidation of (5-cyclopropyl-4-isoxazolyl)[2-(methylthio)-4-(trifluoromethyl)phenyl]-methanone of formula (II) to isoxaflutole of formula (I) by reaction with chloroperbenzoic acid is disclosed both in U.S. patent applications Nos. 2005288516 and 2003055292. Such synthesis method has disadvantages both in term of yield and cost and, therefore, is not applicable for large scale production.

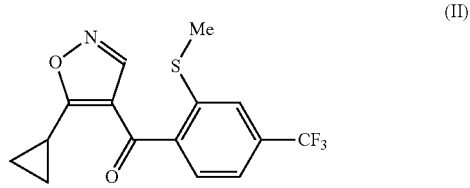 [SMILES: CSc1cc(C(F)(F)F)ccc1C(=O)c1cnoc1C1CC1]

(II)

The oxidation of sulphenyl phenyl-substituted isoxazoles derivatives generally according to U.S. Pat. No. 5,747,424 is conducted using hydrogen peroxide, acetic anhydride and acetic acid or chloroperbenzoic acid in dichloromethane. However, no specific example for producing isoxaflutole is disclosed.

It would be highly desirable to have an improved process for the production of isoxaflutole which is suitable for industrial use, highly efficient, low-cost, environmentally friendly, and provides a high yield in a short reaction time, thereby overcoming the deficiencies of the prior art. The present subject matter provides such a process.

SUMMARY OF THE PRESENT SUBJECT MATTER

The present subject matter provides a process for preparing isoxaflutole of formula (I) wherein the process comprises: admixing (5-cyclopropyl-4-isoxazolyl)[2-(methylthio)-4-(trifluoromethyl)phenyl]-methanone of formula (II) with acetic acid, acetic anhydride, and hydrogen peroxide in the presence of a strong acid. In addition, the present subject matter provides a process for preparing isoxaflutole of formula (I) wherein the process comprises: admixing (5-cyclopropyl-4-isoxazolyl)[2-(methylthio)-4-(trifluoromethyl)phenyl]-methanone of formula (II) with acetic acid and hydrogen peroxide in the presence of a strong acid.

DETAILED DESCRIPTION OF THE PRESENT SUBJECT MATTER

Definitions

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains.

As used herein, the term "mixture" or "combination" refers, but is not limited to, a combination in any physical form, e.g., blend, solution, alloy, or the like.

The term "a" or "an" as used herein includes the singular and the plural, unless specifically stated otherwise. Therefore, the terms "a," "an," or "at least one" can be used interchangeably in this application.

Throughout the application, descriptions of various embodiments use the term "comprising"; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages, or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In this regard, used of the term "about" herein specifically includes ±10% from the indicated values in the range. In addition, the endpoints of all ranges directed to the same component or property herein are inclusive of the endpoints, are independently combinable, and include all intermediate points and ranges.

The compound "(IIa)" refers to the reaction intermediate described below:

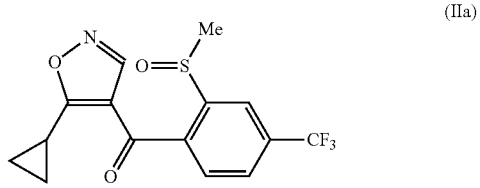 [SMILES: CS(=O)c1cc(C(F)(F)F)ccc1C(=O)c1cnoc1C1CC1]

(IIa)

Process for Preparing Isoxaflutole

The present subject matter provides a process for preparing isoxaflutole of formula (I)

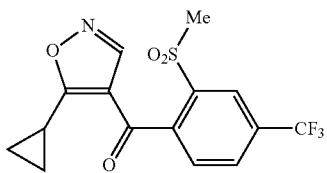

wherein the process comprises: admixing the compound of formula (II)

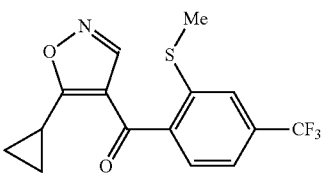

with acetic acid, acetic anhydride, and hydrogen peroxide in the presence of a strong acid.

In another embodiment the present subject matter provides a process for preparing isoxaflutole of formula (I)

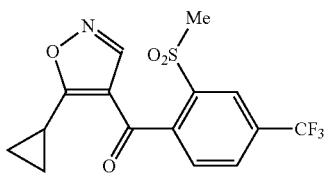

wherein the process comprises: admixing the compound of formula (II)

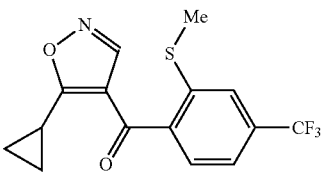

with acetic acid and hydrogen peroxide in the presence of a strong acid.

In another embodiment, the present subject matter provides a process for preparing isoxaflutole of formula (I) wherein the process comprises: admixing (5-cyclopropyl-4-isoxazolyl)[2-(methylthio)-4-(trifluoromethyl)phenyl]-methanone of formula (II) with acetic acid, acetic anhydride, and hydrogen peroxide in the presence of a strong acid; quenching the reaction mixture; isolating the compound of formula (I); and optionally purifying the obtained compound of formula (I).

The present process is advantageous in that it avoids the need for using hazardous and expensive oxidizing reagents. In addition, the process is highly efficient, providing a short reaction time. The present process also avoids the need for using a solvent such as dicloromethane, which is not particularly desirable for industrial implementation due to the hazards associated with such solvent.

In particular, the use of hydrogen peroxide in the present processes reduces the cost of production, simplifies work-up, and minimizes any effluent disposal problems. Further, the present process achieves high yields compared to the methods known in the prior art.

Advantageously, the addition of a strong acid catalyst makes it possible to considerably reduce reaction times while maintaining a high degree of selectivity of oxidation of the compound of formula (II).

Advantageously, the use of acetic acid, hydrogen peroxide and optionally acetic anhydride in the presence of a strong acid does not require the use of any additional organic solvents for the reaction, simplifying the entire process and rendering it economically advantageous.

In one embodiment, the strong acid is selected from the group consisting of sulfuric acid, methanesulfonic acid, benzene sulfonic acid and p-toluenesulfonic acid, hydrochloric acid, nitric acid and a combination thereof. Other strong acids typically used in oxidation reactions may further be useful in the embodied processes.

In a specific embodiment the strong acid is sulfuric acid.

In an embodiment of the present processes, the molar ratio between the strong acid and the compound of formula (II) is from about 1:1 to about 1:100. In another embodiment, the molar ratio between the strong acid and the compound of formula (II) is from about 1:1 to about 1:50. In yet another embodiment, the molar ratio between the strong acid and the compound of formula (II) is from about 1:1 to about 1:10. In a specific embodiment, the molar ratio between the strong acid and compound of formula (II) is about 1:3.5.

In another specific embodiment the molar ratio between the strong acid and compound of formula (II) is about 1:2.2. In yet another specific embodiment the molar ratio between the strong acid and compound of formula (II) is about 1:1.1.

In one embodiment of the present processes, the molar ratio between the sulfuric acid and the compound of formula (II) is from about 1:1 to about 1:100. In another embodiment, the molar ratio between the sulfuric acid and the compound of formula (II) is from about 1:1 to about 1:50. In yet another embodiment, the molar ratio between the sulfuric acid and the compound of formula (II) is from about 1:1 to about 1:10. In a specific embodiment, the molar ratio between the sulfuric acid and the compound of formula (II) is about 1:3.5. In another specific embodiment the molar ratio between the sulfuric acid and compound of formula (II) is about 1:2.2.

In another embodiment of the present processes, the molar ratio between the hydrogen peroxide and the compound of formula (II) is from about 10:1 to about 1:1. In yet another embodiment, the molar ratio between the hydrogen peroxide and the compound of formula (II) is from about 6:1 to about 1:1. In a specific embodiment, the molar ratio between the hydrogen peroxide and the compound of formula (II) is about 5.5:1.

In a further embodiment of the present processes, the molar ratio between the acetic anhydride and the compound of formula (II) is from about 10:1 to about 1:1. In yet another embodiment, the molar ratio between the acetic anhydride and the compound of formula (II) is from about 5:1 to about 1:1. In a specific embodiment, the molar ratio between the acetic anhydride and the compound of formula (II) is 3:1.

In a further, optional, embodiment of the present processes, the reaction may be carried out in an organic solvent selected from the group consisting of monochlorobenzene, polychlorobenzene, toluene, xylene, ethyl acetate, butyl acetate, acetonitrile, N-methylpyrrolidone (NMP) and dimethylacetamide (N,N-DMA), acetone, methanol, ethanol, and a combination thereof. In yet another embodiment, the reaction is carried out without using an organic solvent.

In one embodiment, the oxidation is conducted at a temperature from about 25° C. to about 100° C., more preferably from about 55° C. to about 65° C.

In another embodiment, the hydrogen peroxide is added gradually to the reaction mixture over time. In a specific embodiment, the hydrogen peroxide is added dropwise to the reaction mixture of the (5-cyclopropyl-4-isoxazolyl)[2-(methylthio)-4-(trifluoromethyl)phenyl]-methanone of formula (II) with acetic acid, acetic anhydride, and a strong acid over a period of about 1 hour.

In yet another specific embodiment, the hydrogen peroxide is added dropwise to the reaction mixture of the (5-cyclopropyl-4-isoxazolyl)[2-(methylthio)-4-(trifluoromethyl) phenyl]-methanone of formula (II) with acetic acid, acetic anhydride, and a strong acid over a period of about 0.5 hour.

In this regard, the hydrogen peroxide used in the present processes may be in the form of aqueous solutions. For example, the usual commercial solutions may be used, with a concentration ranging from 30 to 70% by weight. In a specific embodiment, the hydrogen peroxide is used in a concentration of 30% by weight.

In this regard, any excess amounts of the peroxide present may be decomposed by quenching the reaction mixture with a quenching agent selected from the group consisting of sodium metabisulfite, sodium sulfite, sodium bisulfate, and sodium thiosulfate. Preferably, the quenching agent is a solution of sodium sulfite.

The progress of the reaction can be monitored using any suitable method, which can include, for example, chromatographic methods such as, e.g., high performance liquid chromatography (HPLC), thin layer chromatography (TLC), and the like.

In yet another embodiment, the compound of formula (I) can be isolated from the reaction mixture by any conventional techniques well-known in the art. Such isolation techniques can be selected, without limitation, from the group consisting of concentration, extraction, precipitation, cooling, filtration, crystallization, centrifugation, and a combination thereof, followed by drying.

In yet another embodiment, the compound of formula (I) can be optionally purified by any conventional techniques well-known in the art. Such purification techniques can be selected, without limitation, from the group consisting of precipitation, crystallization, slurrying, washing in a suitable solvent, filtration through a packed-bed column, dissolution in an appropriate solvent, re-precipitation by addition of a second solvent in which the compound is insoluble, and a combination thereof.

The following examples illustrate the practice of the present subject matter in some of its embodiments, but should not be construed as limiting the scope of the present subject matter. Other embodiments will be apparent to one skilled in the art from consideration of the specification and examples. It is intended that the specification, including the examples, is considered exemplary only without limiting the scope and spirit of the present subject matter.

EXAMPLE 1

Analytical Method

HPLC analysis was carried out in accordance with the following method and conditions:
Column: Agilent XDB C18 (4.6×150 mm, 5.0 μm)
Temperature: 25° C.

Mobile phase:

| Time | Acetonitrile | 0.1% Formic acid |
|---|---|---|
| 0 min | 30% | 70% |
| 25 min | 75% | 25% |

Flow rate: 1.0 ml/min
Wavelength: 254 nm
HPLC Instrument Details:

| Instrument | Company | Model |
|---|---|---|
| LC-pump | Agilent | G1311A |
| LC-degasser | Agilent | G1322A |
| LC-ALS | Agilent | G1329A |
| LC-TCC | Agilent | G1316A |

EXAMPLE I

A typical experimental procedure is described as follows: the compound of formula II (42 g, 128 mmoles) was added to acetic acid (80 g) and then acetic anhydride (38 g, 370 mmoles) and sulfuric acid (3.7 g, 37.7 mmoles, 0.59 eq) were added. The mixture was heated to 55-60° C., then an aqueous hydrogen peroxide solution (80 g of 30% hydrogen peroxide) was added dropwise over 1 hr, while maintaining the reaction temperature in the range of 55-65° C. The reaction mixture was stirred at 55-60° C. for 3-4 hr. Then, the reaction mixture was cooled to 40° C. and was concentrated under reduced pressure. Water (60 g) was added, stirring was continued for 30 min, and the precipitate was filtered off. Ethanol (60 g) was added and the mixture was heated to reflux for 1.5 hr, and then cooled to 0° C. for 0.5 hr. The precipitate was filtered off and dried in vacuum at 40-50° C. Isoxaflutole was obtained in a 65.9% yield. The reaction was also conducted in the absence of sulfuric acid (referred herein as "blank"). The solutions were analyzed by HPLC and the percentage of the isoxaflutole and the sulfoxide intermediate IIa were monitored during reaction time (Table I).

TABLE I

| | 0.59 eq. $H_2SO_4$ | | blank | |
|---|---|---|---|---|
| Time | (IIa) | IXF | (IIa) | IXF |
| 0.5 hr | 5.26% | 81.05% | 46.35% | 31.15% |
| 1.0 hr | 2.50% | 82.69% | 38.00% | 38.89% |
| 1.5 hr | | | 30.45% | 49.87% |
| 2.0 hr | | | 23.80% | 63.23% |
| 2.5 hr | | | 14.52% | 65.57% |
| 3.0 hr | | | 9.80% | 70.89% |
| 3.5 h | | | 5.82% | 77.50% |

% represents the HPLC area percent.

EXAMPLE II

A solution of acetic acid (90 gr) and the compound of formula (II) (27.3 gr, 83.5 mmol) was mixed with 38 gr acetic anhydride (371 mmol) and 3.7 gr sulfuric acid (37.7 mmol, 0.9 eq). The solution was heated to 55-60° C. 50.0 gr of 30% hydrogen peroxide aqueous solution (441 mmol) was added dropwise through 0.5 h at 60-70° C. The reaction mixture was stirred at 65-70° C. for 1.5 hr, then 150 gr water were added dropwise through 0.5 hr at 65-70° C. and the mixture was stirred at 65-70° C. for 0.5 hr, then cooled to ambient temperature and the precipitate was filtered off, washed with 150 gr water and dried in vacuum at 50° C. 24.15 gr crude product was obtained as an off-white powder. The reaction solution was analyzed by HPLC.

The same procedure described in example 2 was carried out without a strong acid (referred herein as "blank") and with $H_2SO_4$ (0.9 eq and 0.09 eq), p-toluene sulfonic acid (0.9 eq), methane sulfonic acid (0.9 eq) or benzene sulfonic acid (0.9 eq). The results are summarized in Table II.

TABLE II

| Time (h) | Blank | | 0.9 eq $H_2SO_4$ | | 0.09 eq. $H_2SO_4$ | | 0.9 eq. p-toluene sulfonic acid | | 0.9 eq. methane sulfonic acid | | 0.9 eq. benzene sulfonic acid | |
|---|---|---|---|---|---|---|---|---|---|---|---|---|
| | (IIa) % | IXF % | (IIa) % | IXF % | (IIa) % | IXF % | (IIa) % | IXF % | (IIa) % | IXF % | (IIa) % | IXF % |
| 0.5 | 33.80 | 50.49 | 0.08 | 87.86 | 23.4 | 53.19 | 0.22 | 88.05 | 0.15 | 85.24 | 0.28 | 71.35 |
| 1.0 | 19.72 | 65.54 | 0.05 | 89.68 | 1.54 | 83.37 | 0.06 | 89.82 | 0.03 | 87.01 | 0.03 | 89.40 |
| 1.5 | 9.01 | 76.78 | | | 0.12 | 86.51 | 0.03 | 90.29 | | | | |
| 2.0 | 3.65 | 81.23 | | | 0.01 | 87.15 | | | | | | |
| 2.5 | 0.97 | 85.82 | | | | | | | | | | |
| 3.0 | 0.18 | 89.68 | | | | | | | | | | |

Values in the table represent the HPLC area percent (%).

EXAMPLE III 3.7 gr sulfuric acid (36.4 mmol) was added to 120 g of acetic acid solution containing a compound of formula II (23.6 gr, 72.1 mmol) and the reaction mixture was heated to 70° C. 30.0 gr of hydrogen peroxide solution (35%) was added dropwise through 2.5 hr at the temperature range of 65-75° C. The mixture was stirred at 70° C. for 2 hr, and then cooled to ambient temperature. The results are summarized in Table III.

TABLE III

| Time | 1.0 eq $H_2SO_4$ | |
|---|---|---|
| (h) | (IIa) % | IXF % |
| 1.0 | 0.02% | 85.2 |

Values in the table represent the HPLC area percent

As can be seen from the results on tables I, II and III, the reaction is much faster when adding $H_2SO_4$, p-toluene sulfonic acid, methane sulfonic acid or benzene sulfonic acid compared to the reaction without a strong acid (the sample referred herein as "blank"). After 0.5 h reaction the percentage of the product isoxaflutole when adding strong acid such as sulfuric acid (0.9 eq) is much higher (87.86%) compared to the blank example (50.49%). In addition, the percentage of the intermediate IIa is lower after 0.5 h when using the strong acids compare to the "blank" example.

The results show higher efficiency of the reaction when adding strong acid.

While the present subject matter has been shown and described with reference to preferred embodiments thereof, it will be understood by those skilled in the art that many alternatives, modifications and variations may be made thereto without departing from the spirit and scope thereof. Accordingly, it is intended to embrace all such alternatives, modifications, and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:
1. A process for preparing isoxaflutole of formula (I)

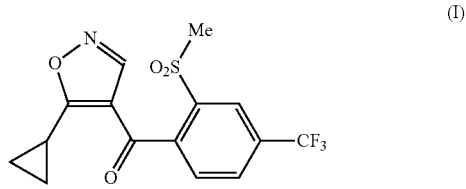

wherein the process comprises:
admixing the compound of formula (II)

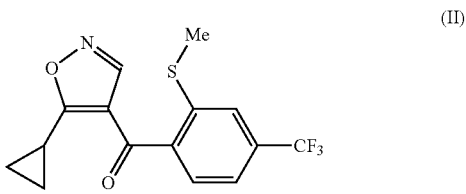

with acetic acid, acetic anhydride, and hydrogen peroxide in the presence of a strong acid.

2. The process of claim 1, further comprising quenching the reaction mixture; isolating the compound of formula (I); and optionally purifying the obtained compound of formula (I).

3. The process of claim 1, wherein the molar ratio between the hydrogen peroxide and the compound of formula (II) is from about 10:1 to about 1:1.

4. The process of claim 3, wherein the molar ratio between the hydrogen peroxide and the compound of formula (II) is about 5.5:1.

5. The process of claim 1, wherein the process is carried out in an organic solvent selected from monochlorobenzene, polychlorobenzene, toluene, xylene, ethyl acetate, butyl acetate, acetonitrile, N-methylpyrrolidone (NMP) and dimethylacetamide (N,N-DMA), acetone, methanol, ethanol, or a combination thereof.

6. The process of claim 1, wherein said strong acid is selected from sulfuric acid, methanesulfonic acid, benzenesulfonic acid, p-toluenesulfonic acid, hydrochloric acid, nitric acid or a combination thereof.

7. The process of claim 6, wherein the molar ratio between the strong acid and the compound of formula (II) is from about 1:1 to about 1:100.

8. The process of claim 1, wherein said strong acid is sulfuric acid.

9. The process of claim 8, wherein the molar ratio between the sulfuric acid and the compound of formula (II) is from about 1:1 to about 1:100.

10. The process of claim 8, wherein the molar ratio between the sulfuric acid and the compound of formula (II) is about 1:3.5.

11. The process of claim 8, wherein the molar ratio between the sulfuric acid and the compound of formula (II) is about 1:2.2.

12. The process of claim 1, wherein the process is conducted at a temperature ranging from about 25° C. to about 100° C.

13. The process of claim 12 wherein said strong acid is selected from sulfuric acid, methanesulfonic acid, benzenesulfonic acid, p-toluenesulfonic acid, hydrochloric acid, nitric acid or a combination thereof.

14. The process of claim 12, wherein the molar ratio between the strong acid and the compound of formula (II) is from about 1:1 to about 1:100.

15. The process of claim 12, wherein said strong acid is sulfuric acid.

16. The process of claim 12, wherein the molar ratio between the sulfuric acid and the compound of formula (II) is about 1:2.2.

17. The process of claim 12, wherein the molar ratio between the hydrogen peroxide and the compound of formula (II) is from about 10:1 to about 1:1.

18. The process of claim 12, wherein the process is carried out in an organic solvent selected from monochlorobenzene, polychlorobenzene, toluene, xylene, ethyl acetate, butyl acetate, acetonitrile, N-methylpyrrolidone (NMP) and dimethylacetamide (N,N-DMA), acetone, methanol, ethanol, or a combination thereof.

19. The process of claim 8, wherein the process is conducted at a temperature ranging from about 25° C. to about 100° C.

\* \* \* \* \*